Sept. 10, 1968 A. PERRY Plant Pat. 2,831
ROSE PLANT
Filed Dec. 5, 1966
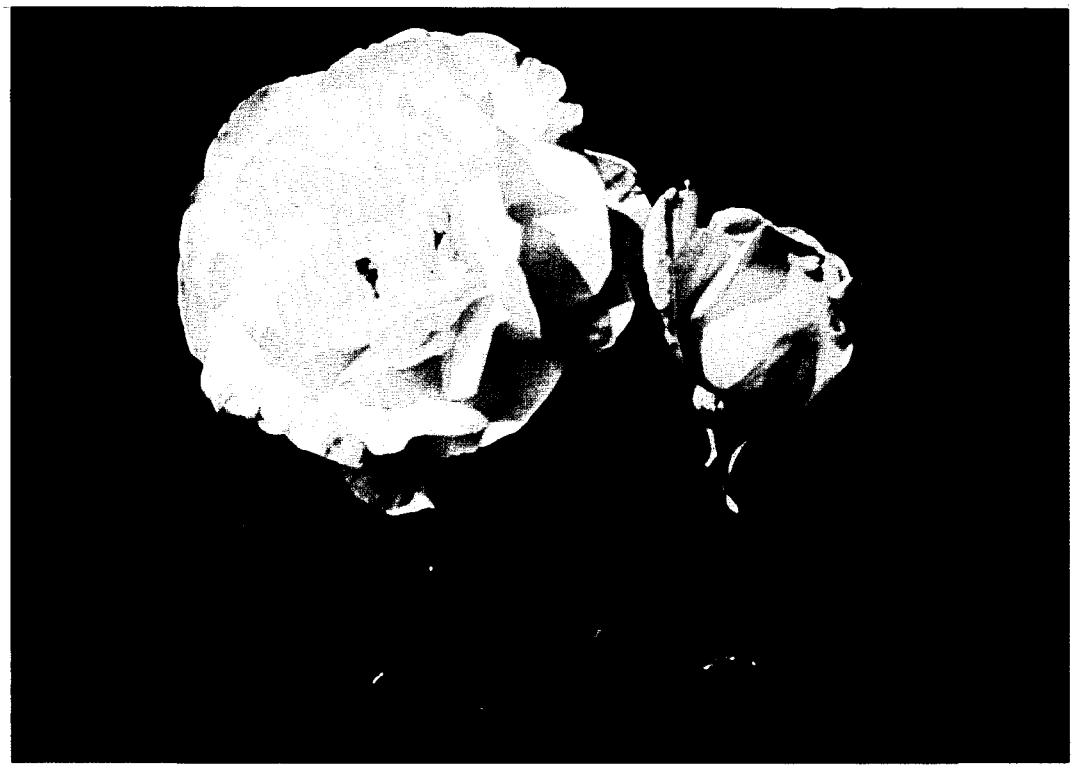
INVENTOR.
ANTHONY PERRY
BY J. F. Cuneo
ATTORNEY.

United States Patent Office

Plant Pat. 2,831
Patented Sept. 10, 1968

2,831
ROSE PLANT

Anthony Perry, Garden Grove, Calif., assignor to Henry A. Conklin, McFarland, Calif.

Filed Dec. 5, 1966, Ser. No. 599,329
1 Claim. (Cl. Plt.—11)

This invention relates to a new and distinct variety of rose plant that is generally classified as a hybrid tea rose.

This new variety resulted from cross-breeding Fred Howard, a patented rose, U.S. Plant Patent No. 1,006, with Queen Elizabeth, a patented rose, U.S. Plant Patent No. 1,259, after numerous experiments conducted by me at Garden Grove, Calif. The original plant was produced by me in June 1956, using Fred Howard as the seed parent and Queen Elizabeth as the pollen parent.

The flowers produced by the new variety of rose plant are coral pink when the buds have fully opened and form large sized blooms that are borne at the end of medium length stems. The flowers are produced in abundance during the growing season that generally extends from February to November and usually well into the latter in the coastal region of southern California. The plant forms a large, well branched, upright bush that has large leaves that are considerably larger than most rose leaves; the bush reaches a height of as much as six and one half feet.

In comparing the blooms of the new variety with those of its pollen parent Queen Elizabeth, the flowers of the new variety are Azalea Pink on the under side and are Chinese Coral on the upper side of the petals, while those of the pollen parent are Carmine Rose. The blooms are borne on a single stem as a hybrid tea rose. Compared to its seed parent Fred Howard, the foliage of the new variety is much larger and a lighter green. The plant produces a greater abundance of flowers on stems that vary between 12" to 18" in length and are Azalea Pink on the underside and Chinese Coral on the upper side of the petals whereas the flowers of the seed parent are a buff yellow. The plant is best described as hardy and exhibits a vigorous upright habit, some of the plants have reached a height of six and one-half feet.

The new variety belongs to the outdooor bush type and is used for garden ornamentation and cut flowers. The plant has been reproduced asexually by budding performed in Garden Grove Calif. as well as in McFarland, Calif. The resulting plants and the flowers reproduced true with all of the distinguishing characteristics being transmitted through the succeeding propagations of the variety; the plant cannot be reproduced true from seed.

The accompanying illustration in full color shows a typical specimen of the blooms produced by this new variety. The colors are as true as it is possible to reproduce them by using this type of color representation.

A detailed description of the new variety of rose follows and in order to facilitate identification of the important colors described in the specification, the designations adopted by the British Horticultural Colour Charts have been followed.

The new rose belongs to the outdoor bush type and is of the so-called hybrid tea class. Its beautiful pink large sized blooms on the end of fairly long stems make this rose particularly desirable for cut flowers and for ornamenting gardens.

*The flower*

Locality where grown and observed: Garden Grove, Calif.; and McFarland, Calif.

Flowers borne: The flowers are borne usually as single flowers on fairly long stems that vary from twelve to eighteen inches in length.

Number of blooms: When grown outdoors the plant produces an abundance of flowers, there being between twenty to fifty blooms on the plant at one time.

Continuity: The plant blooms from early spring to and sometimes through the month of November. Extremely warm weather has a tendency of reducing the size of the blooms.

Fragrance: This variety produces flowers that have a slight rose fragrance.

Bud:

*Peduncle.*—Length—from one and one-half to two inches. Color—green.

*Before calyx breaks.*—Size—about three-quarters of an inch in diameter. Form—the bud is best described as ovoid.

*As calyx breaks.*—Color—dark rose pink. Sepals: shape—spear shaped with a rounded base; size—the sepals can be as much as one and one-half inches in length.

*As first petal opens.*—Size—the petals are quite large. Color—upper side—the predominant color is Chinese Coral 614/2; underside—the color is Azalea Pink 618/2; base of petal—the petals shade to Primrose Yellow 601 at and near the base. Form—the petals are orbiculate.

Bloom:

*Size.*—The flowers are from five and one-half to six inches in diameter.

*Petalage.*—The number of petals varies from 50 to 60.

*Form.*—Globular with high center. The inner petals are smaller than the outer petals.

*Petals.*—Shape—the petals are substantially round at the tip with the base acute; the tip is usually retuse having a centrally positioned W-shaped notch. Size—matured petals can be as much as 2½" across. Color—upper side—the upper side of the petals is Chinese Coral 614/2; under side—the under side of the petals is Azalea Pink 618/2; the petals shade to Primrose Yellow 601 at the base. Texture—the petals have a leathery appearance.

*General color effect.*—Coral Pink inside with rose pink outside.

*Behaviour.*—The petals drop off clean, the flowers are somewhat stunted in very warm weather.

*Flower longevity.*—The flowers last from five to six days.

*Reproductive organs*

Stamens: Average in number.

Filaments: Filaments are about one-quarter of an inch long. Color—filaments are golden colored.

Anthers: Anthers are not prominent. Color—golden yellow.

Pollen:

*Quantity.*—Moderate.

*Color.*—Golden yellow.

Pistils: Numerous.

Styles: Not prominent.

Stigma: Not prominent.

Ovaries: Ovaries are not visible, being enclosed in calyx.

Hips:

*Length.*—From one-half to three-quarters inches in length.

*Form.*—Oblong.

*Color.*—Light green.

Seeds: Average in number. Do not set freely.

*The plant*

Foliage: Compound, odd pinnate leaves having an average of three leaflets generally; a few leaves have five leaflets.

*Quantity.*—Normal.

*Leaflets.*—Shape—leaflets are best described as ovate with a tip that is substantially acuminate. The base of each leaflet is between obtuse and truncate; the margin of the leaflet is surrulate. Size—the leaflets are in general larger than ordinary with some of the leaflets having a length of four inches and a width of two and three-quarter inches. Color: upper-side—Spinach Green o960/1; underside—Spinach Green o960/3.

*Young leaflets.*—Color—young leaflets have approximately the same color as the mature leaflets with the exception that the new leaflets have a definite reddish coloration that disappears when the leaflets have matured.

*Type.*—Imparipinnate.

*Stipules.*—Stipules are flaring and are up to five-eighths inch in length.

*Growth.*—Habit and height—the plant is vigorous, upright and well branched; the plant reaches as much as six and one half feet in height.

*Canes.*—The diameter of the canes varies from three-quarter to one inch in diameter at the base.

*Main stems.*—Length—from four to six and one-half feet long. Color—light to medium green.

*Prickles (large).*—Size and spacing—the prickles are from ⅜″ to ½″ in length. These are widely spaced.

*Prickles (small).*—None.

*Branches.*—Color—light green. Shape—predominantly vertical. Thorns: number and size—thorns are moderate in number being widely spaced; these vary from ⅜″ to ½″ in length.

*New shoots.*—Color—Bronzy reddish green. Large and small prickles—none.

Having described my invention, I claim:

1. The new and distinct variety of rose plant of the class designated as hybrid tea roses, substantially as shown and described, characterized particularly as to novelty by the globular, high centered, large sized blooms that have large petals that are Chinese Coral on the upper side and Azalea Pink on the underside, said blooms borne as single flowers on medium to long stems, by the slight rose fragrance of the blooms that is more noticeable in cooler weather, by the tall, vigorous upright growth of the plant, and by the very large-sized leaflets.

No references cited.

ROBERT E. BAGWILL, *Primary Examiner.*